United States Patent
Murray et al.

(10) Patent No.: US 6,509,040 B1
(45) Date of Patent: Jan. 21, 2003

(54) FAST DISPERSING DOSAGE FORMS ESSENTIALLY FREE OF MAMMALIAN GELATIN

(75) Inventors: Owen James Murray, Franklin Township, Somerset County, NJ (US); Richard Green, Kent (GB); Patrick Kearney, Swindon (GB); Leon Paul Grother, Swindon (GB)

(73) Assignee: R.P. Scherer Corporation, Basking Ridge, NJ (US)

( * ) Notice: Subject to any disclaimer, the term of this patent is extended or adjusted under 35 U.S.C. 154(b) by 0 days.

(21) Appl. No.: 09/887,604

(22) Filed: Jun. 22, 2001

(51) Int. Cl.⁷ .............................. A61K 9/14; A61F 13/00
(52) U.S. Cl. ................... 424/489; 424/400; 424/434; 424/486; 424/488; 424/490
(58) Field of Search ...................... 424/490, 488, 424/434, 400, 489, 486

(56) References Cited

U.S. PATENT DOCUMENTS

| | | |
|---|---|---|
| 3,885,026 A | 5/1975 | Heinemann et al. |
| 4,134,943 A | 1/1979 | Knitsch et al. |
| 4,551,177 A | 11/1985 | Trubiano et al. |
| 4,591,507 A | 5/1986 | Bodor et al. |
| 4,946,684 A * | 8/1990 | Blank et al. ............ 424/441 |
| 5,079,018 A | 1/1992 | Ecanow |
| 5,298,261 A | 3/1994 | Pebley et al. |
| 5,382,437 A | 1/1995 | Ecanow |
| 5,466,464 A | 11/1995 | Masaki et al. |
| 5,595,761 A | 1/1997 | Allen, Jr. et al. |
| 5,629,003 A | 5/1997 | Horstmann et al. |
| 5,631,023 A | 5/1997 | Kearney et al. |
| 5,747,068 A | 5/1998 | Mendizabal |
| 5,753,254 A | 5/1998 | Khan et al. |
| 5,843,347 A | 12/1998 | Nguyen et al. |

FOREIGN PATENT DOCUMENTS

| | | |
|---|---|---|
| EP | 0159631 | 10/1985 |
| EP | 0599767 | 6/1994 |
| EP | 0693281 | 7/1994 |
| GB | 2172006 | 9/1986 |
| WO | WO 93/13758 | 7/1993 |
| WO | WO 91/04757 | 4/1994 |
| WO | WO 94/14422 | 7/1994 |

OTHER PUBLICATIONS

US 5,120,549, 6/1992, Gole et al. (withdrawn)

* cited by examiner

Primary Examiner—Thurman K. Page
Assistant Examiner—Micah-Paul Yang
(74) Attorney, Agent, or Firm—Donald O. Nickey

(57) ABSTRACT

The present invention relates to fast dispersing solid dosage forms that preferably dissolve in the oral cavity within sixty (60), more preferably within thirty (30), most preferably within ten (10) seconds. A novel feature of the solid dosage forms according to the invention reside in the fact that the composition is essentially free or absolutely free of mammalian gelatin. It has been discovered that the use of certain modified starches at concentrations from 20 to 90% by weight of the solid dosage form prepares dosage forms that are mechanically and chemically stable and are able to deliver higher concentrations of an active ingredient than the heretofore utilized gelatin based fast dispersing solid dosage forms. Further, the solid dosage forms according to the invention are obtainable by removing a solvent, such as water, from a mixture comprising an active ingredient, a modified starch and a matrix forming agent via freeze drying.

8 Claims, No Drawings

FAST DISPERSING DOSAGE FORMS ESSENTIALLY FREE OF MAMMALIAN GELATIN

TECHNICAL FIELD

This invention relates to a pharmaceutical composition for oral administration in the form of a fast dispersing dosage form. The novel dosage form is essentially free of mammalian gelatin and comprises at least one matrix forming agent and a lactose modified starch.

BACKGROUND OF THE INVENTION

The most common pharmaceutical dosage form is the tablet. The main limitations of tablets include poor patient compliance due to difficulty in swallowing tablets and lack of bioavailability of the active through the ineffective dissolution of the tablet. Thus, there is a need in the medical community for rapidly soluble dosage forms. A number of approaches have been utilized to overcome the shortcomings of tablets, including effervescent tablets, chewable tablets, disintegrants, and wicking agents.

Most recently, fast dispersing dosage forms, which are designed to release the active ingredient in the oral cavity, have been formulated using rapidly soluble gelatin-based matrices. These dosage forms are well known and can be used to deliver a wide range of drugs. Most fast dispersing dosage forms utilize gelatin as a carrier or structure-forming agent. Typically, gelatin is used to give sufficient strength to the dosage form to prevent breakage during removal from packaging, but once placed in the mouth, the gelatin allows immediate dissolution of the dosage form.

Gelatin B. P., which is normally utilized in such formulations, is defined as a protein obtained by partial hydrolysis of animal collagenous tissues, such as skins, tendons, ligaments and bones. However, such mammalian-derived gelatin has a bland taste and thus necessitates the use of sweeteners and flavors in such fast dispersing dosage forms to mask the taste of the active ingredient. When conventional mammalian derived gelatin is used in the production of such fast dispersing dosage forms, it is necessary to heat the gelatin solution in order to effect solution. This heating step increases processing times and incurs heating costs thereby increasing the overall costs of the process.

Conventional processing can require holding times of up to 48 hours. It has been observed that over this time the viscosity of the gelatin-based mixture can increase, leading to processing difficulties. Furthermore, the use of mammalian gelatin produces dosage forms that readily absorb water and this can lead to shrinkage of the dosage form during normal storage periods.

Another known problem associated with gelatin-based fast dissolving dosage forms is the lack of homogeneity and sedimentation of the liquid mix during holding periods, as some mixtures incorporate the active substance as suspended particles. The use of mammalian-derived gelatin results in sedimentation of the active due to mammalian gelatin's low viscosity. One benefit of the present invention is that the modified starches disclosed herein substantially overcome the homogeneity and sedimentation problems associated with mammalian gelatin.

Another benefit associated with the use of modified starches in the preparation of fast dissolving dosage forms resides in the discovery that the modified starch dosage form is capable of higher drug loadings. This is beneficial in that for a given dose of active, the modified starch dosage form may be substantially smaller than the conventional gelatin dosage form.

Other materials have been tried in place of gelatin in fast dispersing dosage forms but while they may form robust products (reduced propensity to cracking and breaking) they generally disperse slowly or form a gummy mass in the mouth. It has now been found that modified starches may be used instead of mammalian-derived gelatin to prepare fast dispersing dosage forms.

According to the present invention there is therefore provided a pharmaceutical composition for oral administration in the form of a fast dispersing dosage form designed to release an active ingredient rapidly in the oral cavity characterized in that the essentially gelatin free composition comprises a modified starch and at least one matrix forming agent.

The invention provides the possibility of reducing or preferably eliminating gelatin from fast dispersing dosage forms (FDDF). Modified starches may be used as the primary structure forming agent in FDDF's to form physically robust products while maintaining the desired rapid dispersion characteristics of the products. By suitable selection of the modified starch it is possible to obtain particularly desirable properties of cold water solubility, no change in solution viscosity with time and improved stability and physical strength of the dosage form. The use of modified starch allows the level of sweeteners/flavorants, which have previously been used to improve the taste of the dosage form, to be reduced or eliminated. The use of a botanical source material as opposed to the use of an animal source material also has the benefit of eliminating exposure to agents such as BSE.

Starch can be considered a condensation polymer of glucose. These glucose constituents are present as anhydroglucose units (AGU). If starch is treated with either acids or certain enzymes it can be totally degraded, by hydrolysis of glycosidic bonds, into its constituent glucose units. Most starches consist of two types of glucose polymers, each having a wide range of molecular sizes:

(i) a linear chain molecule termed amylose, which can contain up to 6,000 glucose units linked by 1 to 4 linkages and, (ii) a highly branched polymer termed amylopectin, consisting of short chains (10 to 60 glucose units) connected by $\mu$-1,6-linkages.

The glucose units of starch molecules contain a primary hydroxyl group on carbon-6 and a secondary hydroxyl group on carbon-2 and carbon-3. Starch molecules have a multitude of hydroxyl groups, which impart hydrophilic properties to the starch and lead to the dispersibility of starch on heating with water. However, these hydroxyl groups also tend to attract to each other, forming hydrogen bonds between adjacent starch molecules and preventing dissolution in cold water.

Native starch can be altered by physical, chemical or enzymatic treatment to alter their properties or impart new ones. Properties of these modified starches include solid-viscosity relationships, gelatinization and cooking characteristics, resistance of breakdown in viscosity by acids, heat and/or mechanical shear, ionic character and hydrophilic character.

A range of modified starches are commercially available and useful in the present invention and include:

Pregelatinized starches, produced by drum drying or extrusion;

Low-viscosity starches, produced by controlled hydrolysis of glycosidic bonds;

Dextrins, produced by roasting dry starch in the presence of a small amount of acid;

Acid modified starches, produced by suspension in dilute acid until the required viscosity is reached;

Oxidized starches, oxidizing agents cause the introduction of carbonyl or carboxyl groups, wherein depolymerization occurs, leading to decreased retrogradation and gelling capacities;

Enzymatically modified starch, produced by controlled enzyme degradation to attain required physicochemical properties;

Crosslinked starches, bi- or polyfunctional reagents react with hydroxyl groups to form crosslinks, examples of specific reagents include phosphorus oxychloride, sodium trimetaphosphate and epichlorohydrin; and Stabilized starches, starches are reacted with etherifying or esterifying reagents in the presence of an alkaline catalyst to give a wide range of products.

BACKGROUND ART

U.S. Pat. No. 5,120,549 discloses a fast dispersing dosage form which is prepared by first solidifying a matrix-forming system dispersed in a first solvent and subsequently contacting the solidified matrix with a second solvent that is substantially miscible with the first solvent at a temperature lower than the solidification point of the first solvent, the matrix-forming elements and active ingredient being substantially insoluble in the second solvent, whereby the first solvent is substantially removed resulting in a fast dispersing dosage form.

U.S. Pat. No. 5,079,018 discloses a fast dispersing dosage form which comprises a porous skeletal structure of a water soluble, hydratable gel or foam forming material that has been hydrated with water, rigidified in the hydrated state with a rigidifying agent and dehydrated with a liquid organic solvent at a temperature of about 0° C. or below to leave spaces in place of the hydration liquid.

Published International Application No. WO 93/12769 (PCT/JP93/01631) describes fast dispersing dosage forms of very low density formed by gelling, with agar, aqueous systems containing the matrix-forming elements and active ingredient, and then removing water by forced air or vacuum drying.

U.S. Pat. No. 5,298,261 discloses fast dispersing dosage forms which comprise a partially collapsed matrix network that has been vacuum-dried above the collapse temperature of the matrix. However, the matrix is preferably at least partially dried below the equilibrium freezing point of the matrix.

Published International Application No. WO 91/04757 (PCT/US90/05206) discloses fast dispersing dosage forms, which contain an effervescent disintegration agent, designed to effervesce on contact with saliva to provide rapid disintegration of the dosage form and dispersion of the active ingredient in the oral cavity.

U.S. Pat. No. 5,595,761 discloses a particulate support matrix for use in making a rapidly dissolving tablet, comprising;

a first polypeptide component having a net charge when in solution, e.g. non-hydrolyzed gelatin;

a second polypeptide component having a net charge of the same sign as the net charge of the first polypeptide component when in solution e.g. hydrolyzed gelatin; and a bulking agent, and wherein the first polypeptide component and the second polypeptide component together comprise about 2% to 20% by weight of the particulate support matrix and wherein the bulking agent comprises about 60% to 96% by weight of the particulate support matrix; and wherein the second polypeptide component has a solubility in aqueous solution greater than that of the first polypeptide component and wherein the mass (mass ratio of the first polypeptide component to the second polypeptide component) is from about 2:1 to about 1:14; and wherein when the support matrix is introduced into an aqueous environment the support matrix disintegrates within less than about 20 seconds.

EP-B-0690747 describes particles comprising an excipient forming a matrix and at least one active ingredient uniformly distributed in the mass of the matrix which are prepared by a process comprising the steps of preparing an homogeneous pasty mixture with a viscosity below 1 Pa.s, measured at room temperature (15–20° C.), from at least one active ingredient, a physiologically acceptable hydrophilic excipient and water; extruding the resulting homogeneous mixture and cutting the extrudate to give moist particles; freezing the resulting particles as they fall under gravity through a stream of inert gas at a temperature below 0° C.; and drying the particles by freeze drying.

Australian Pat. No. 666666 discloses a multiparticulate tablet having a mixture of excipients in which the active substance is present in the form of coated microcrystals or optionally coated microgranules. Such tablets disintegrate in the mouth in an extremely short time, typically less than 60 seconds.

U.S. Pat. No. 5,382,437 discloses a porous carrier material having sufficient rigidity for carrying and administering an active material which is capable of rapid dissolution by saliva and which is formed by freezing a liquified ammonia solution comprising liquid ammonia, a liquid ammonia-soluble gel or foam material and a rigidifying agent for the gel or foam material selected from the group consisting of a monosaccharide, a polysaccharide and combinations thereof, and deammoniating the frozen material thus formed by causing material transfer of ammonia from the frozen state to the gas state thereby leaving spaces in the carrier material in place of the frozen ammonia.

Published International Application No. WO 93/13758 (PCT/US92/07497) describes tablets of increased physical strength which are prepared by combining and compressing a meltable binder, excipients and a pharmaceutically active agent into a tablet, melting the binder in the tablet and then solidifying the binder. In one embodiment, a disintegrating agent is utilized to increase the disintegration rate of the tablet after oral intake. In another embodiment, a volatile component is used to form porous tablets. Some embodiments disintegrate in the mouth in less than 10 seconds.

U.S. Pats. Nos. 3,885,026 and 4,134,943 also disclose fast dispersing porous tablets and a method for increasing their physical strength by first compressing the tablet and then volatilizing a readily volatile solid adjuvant incorporated in the tablet to attain the desired porosity.

Published International Application No. WO 94/14422 describes a process for drying frozen discrete units in which the solvent is removed under conditions whereby the solvent is evaporated from the solid through the liquid phase to a gas, rather than subliming from a solid to a gas as in lyophilization. This is achieved by vacuum drying at a temperature below the equilibrium freezing point of the composition at which point the solvent (such as water) changes phase.

EP-0693281 to Lilly S. A. relates to pharmaceutical formulations of fluoxetine or acid addition salts thereof that are placed in dispersible tablets by direct compression. This reference does disclose the use of sodium starch glycolate as a disintegrant. The sodium starch glycolate is used in this reference at concentrations exceeding 5% by weight, preferably at concentrations between 9.5% and 17%. This reference does not disclose a fast dispersing solid dosage form that contains at least 20% by weight of at least one modified starch and a process for the preparation of the dosage form wherein a solvent is removed from a mixture comprising an active ingredient, a modified starch and a matrix forming agent.

EP-0599767 relates to a procedure for the preparation of dispersible Diclofenac tablets. The procedure is characterized by the compression of a mixture consisting of granules containing a hydrophilic lubricant and a disintegrant, the active ingredient and other excipients. The excipients include microcrystalline cellulose, corn starch and lactose. The examples also indicate the use of carboxymethyl starch. This reference fails to suggest or disclose a fast dispersing solid dosage form that contains at least one active ingredient, at least one modified starch at a concentration of from 20% to 90% by weight of the solid dosage form and at least one matrix forming agent. Further, this reference teaches away from the instant invention's process of forming the solid dosage form wherein a solvent is removed from the mixture by freeze drying.

EP-0159631 to National Starch & Chemical Corporation relates to compressible starches as binders for tablets or capsules. This reference discloses a number of chemically modified starches that are suitable for use as binders in tableting operations, especially direct compression and which are likewise useful as binders, diluents and the like for capsule filling operations. This references does not suggest nor disclose the use of such modified starches in fast dispersing solid dosage forms that are obtainable by removing a solvent from a mixture comprising an active ingredient, a modified starch and a matrix forming agent.

GB-2172006 relates to excipients for use in compression molding of tablets. This reference discloses excipients that are prepared by dispersing a cellulose powder and hydroxypropyl starch powder in an aqueous solution and thereafter spray drying the dispersion. This preparation is disclosed as being useful in compression molding of tablets. There is no suggestion nor disclosure of a fast dispersing solid dosage form that contains at least one modified starch at concentrations of from 20% to 90% by weight of the dosage form and wherein the dosage form is obtainable by removing a solvent from a mixture comprising an active ingredient, a modified starch and a matrix forming agent.

U.S. Pat. No. 5,629,003 to Horstmann et al. relates to rapidly disintegrating sheet-like preparations that comprise 20% to 60% of at least one film forming agent, i.e., mannitol, 2% to 40% by weight of at least one gel forming agent, i.e., modified starch, an active substance and up to 40 weight % of at least one inert filling agent. The product of this reference is spread on siliconized paper and dried at 80° C. for 15 minutes. This reference does not suggest nor disclose a fast dispersing solid dosage form that contains at least one modified starch at concentrations of from 20% to 90% by weight of the dosage form and where the solid dosage form is obtained by removing a solvent from a mixture comprising an active ingredient, a modified starch and a matrix forming agent.

A Chemical Abstracts article entitled "Preparation of Emulsifying Agents for Pharmaceuticals, Cosmetics and Foods", Vol. 110, No. 10, Abstract No. 82495, discloses the use of modified starches as an emulsifying agent in pharmaceuticals. This reference makes no suggestion nor disclosure of a fast dispersing solid dosage form that comprises at least one modified starch at a concentration of from 20% to 90% by weight, wherein the dosage form is obtained by removing a solvent from a mixture comprising an active ingredient, the modified starch and a matrix forming agent.

SUMMARY OF THE INVENTION

There is disclosed a fast dispersing solid dosage form designed to release an active ingredient rapidly in the oral cavity characterized in that said dosage form is essentially free of mammalian gelatin and comprises:

at least one active ingredient;
at least one modified starch at a concentration of from 20 to 90% by weight of said solid dosage form; and
at least one matrix forming agent;
wherein said solid dosage form is obtainable by removing a solvent from a mixture comprising said active ingredient, said modified starch and said matrix forming agent.

In one embodiment of the invention, the solid dosage form comprises at least one modified starch selected from the group consisting of starches that have had their hydroxyl groups esterified, hydroxypropyl di-starch phosphate, an enzymatically modified starch, a pregelatinized di-starchphosphate, hydroxyethyl starch, a pregelatinized acetylated di-starch phosphate, and a pregelatinized purified starch.

In a preferred embodiment, the solid dosage form according to the invention comprises 50 to 90% by weight of the modified starch.

While many specific examples are provided on the useful modified starches, a general characteristic of the useful modified starches in the fast dispersing solid dosage form according to the invention is that they are readily soluble or dispersible in water at ambient temperature. Another benefit associated with the modified starches useful in the present invention is that the mixture of the active, the modified starch and the matrix forming agent exhibits a fairly consistent viscosity over a period of about 24 hours. The preferred solvent in accordance with the invention is water. The preferred matrix forming agent is mannitol.

The fast dispersing solid dosage forms according to the invention may also contain coloring agents, flavoring agents, excipients, multiple therapeutic agents and the like. In one preferred embodiment according to the invention, the removal of the solvent from the mixture is preferably carried out by freeze drying.

DETAILED DESCRIPTION OF THE INVENTION

As used herein and in the claims, the term "fast dispersing dosage form (FDDF)" refers to compositions which disintegrate/disperse within 1 to 60 seconds, preferably 1 to 30 seconds, more preferably 1 to 10 seconds and particularly 2 to 8 seconds, of being placed in the oral cavity. The dosage form of the present invention is similar to the dosage forms described in U.K. Pat. No. 1548022, that is, a solid fast dispersing dosage form comprising a network of the active ingredient and a water-soluble or water-dispersible carrier, which is inert towards the active ingredient, the network having been obtained by subliming solvent from a composition in the solid state, that composition comprising the active ingredient and a solution of the carrier in a solvent. The point of distinction being that the modified starch is used as the carrier in place of the conventional mammalian gelatin.

The fast dispersing dosage form according to the invention may also contain, in addition to the active ingredient and modified starch, other matrix forming agents and secondary components. Matrix forming agents suitable for use in the present invention include materials derived from animal or vegetable proteins, such as non-mammalian gelatins, dextrins and soy, wheat and psyllium seed proteins; gums such as acacia, guar, agar, and xanthan; polysaccharides; alginates; carboxymethylcelluloses; carrageenans; dextrans; pectins; synthetic polymers such as polyvinylpyrrolidone; and polypeptide/protein or polysaceharide complexes such as gelatin-acacia complexes.

Matrix forming agents suitable for use in the present invention include sugars such as mannitol, dextrose, lactose, galactose and trehalose; cyclic sugars such as cyclodextrin; inorganic salts such a s s odium phosphate, sodium chloride and aluminum silicates; and amino acids having from 2 to 12 carbon atoms such as a glycine, L-alanine, L-aspartic acid, L-glutamic acid, L-hyd roxyprsline, L-isoleucine , L-leucine and L-phenylalanine.

One or m ore matrix forming agents may be incorporated into the solution or suspension prior to solidification. The matrix forming agent may be present in addition to a surfactant or to the exclusion of a surfactant. In addition to forming the matrix, the matrix forming agent may aid in maintaining the dispersion of any active ingredient within the solution, suspension or mixture. This is especially helpful in the case of active agents that are not sufficiently soluble in water and must, therefore, be suspended rather than dissolved.

Secondary components such as preservatives, antioxidants, surfactants, viscosity enhancers, coloring agents, flavoring agents, pH modifiers, sweeteners or taste-masking agents may also be incorporated into the composition. Suitable coloring agents include red, black and yellow iron oxides and FD & C dyes such as FD & C Blue No. 2 and FD & C Red No. 40. Suitable flavoring agents include mint, raspberry, licorice, orange, lemon, grapefruit, caramel, vanilla, cherry and grape flavors and combinations of these. Suitable pH modifiers include citric acid, tartaric acid, phosphoric acid, hydrochloric acid, maleic acid and sodium hydroxide. Suitable sweeteners include aspartame, acesulfame K and thaumatin. Suitable taste-masking agents include sodium bicarbonate, ion-exchange resins, cyclodextrin inclusion compounds, adsorbates or microencapsulated actives.

In general the modified starch will comprise from 5% to 99.5% by weight solids of the FDDF, normally 20% to 90%, usually 50 to 90%.

Any drug may be used as the active ingredient in the composition of the present invention. Examples of suitable drugs include but are not limited to those listed below:

Analgesics and Anti-inflammatory Agents: aloxiprin, auranofin, azapropazone, benorylate, diflunisal, etodolac, fenbufen, fenoprofen calcim, flurbiprofen, ibuprofen, indomethacin, ketoprofen, meclofenamic acid, mefenamic acid, nabumetone, naproxen, oxaprozin, oxyphenbutazone, phenylbutazone, piroxicam, sulindac.

Anthelmintics: albendazole, bephenium hydroxynaphthoate, cambendazole, dichlorophen, ivermectin, mebendazole, oxamniquine, oxfendazole, oxantel embonate, praziquantel, pyrantel embonate, thiabendazole.

Anti-arrhythmic Agents: amiodarone HCl, disopyramide, flecainide acetate, quinidine sulphate.

Anti-bacterial Agents: benethamine penicillin, cinoxacin, ciprofloxacin HCl, clarithromycin, clofazimine, cloxacillin, demeclocycline, doxycycline, erythromycin, ethionamide, imipenem, nalidixic acid, nitrofurantoin, rifampicin, spiramycin, sulphabenzamide, sulphadoxine, sulphamerazine, sulphacetamide, sulphadiazine, sulphafurazole, sulphamethoxazole, sulphapyridine, tetracycline, trimethoprim.

Anti-coagulants: dicoumarol, dipyridamole, nicoumalone, phenindione.

Anti-depressants: amoxapine, ciclazindol, maprotiline HCl, mianserin HCl, nortriptyline HCl, trazodone HCl, trimipramine maleate.

Anti-diabetics: acetohexamide, chlorpropamide, glibenclamide, gliclazide, glipizide, tolazamide, tolbutamide.

Anti-epileptics: beclamide, carbamazepine, clonazepam, ethotoin, methoin, methsuximide, methylphenobarbitone, oxcarbazepine, paramethadione, phenacemide, phenobarbitone, phenytoin, phensuximide, primidone, sulthiame, valproic acid.

Anti-fungal Agents: amphotericin, butoconazole nitrate, clotrimazole, econazole nitrate, fluconazole, flucytosine, griseofulvin, itraconazole, ketoconazole, miconazole, natamycin, nystatin, sulconazole nitrate, terbinafine HCl, terconazole, tioconazole, undecenoic acid.

Anti-gout Agents: allopurinol, probenecid, sulphinpyrazone.

Anti-hypertensive Agents: amlodipine, benidipine, darodipine, dilitazem HCl, diazoxide, felodipine, guanabenz acetate, indoramin, isradipine, minoxidil, nicardipine HCl, nifedipine, nimodipine, phenoxybenzamine HCl, prazosin HCL, reserpine, terazosin HCl.

Anti-malarials: amodiaquine, chloroquine, chlorproguanil HCl, halofantrine HCl, mefloquine HCl, proguanil HCl, pyrimethamine, quinine sulphate.

Anti-migraine Agents: dihydroergotamine mesylate, ergotamine tartrate, methysergide maleate, pizotifen maleate, sumatriptan succinate.

Anti-muscarinic Agents: atropine, benzhexol HCl, biperiden, ethopropazine HCl, hyoscine butyl bromide, hyoscyamine, mepenzolate bromide, orphenadrine, oxyphencylcimine HCl, tropicamide.

Anti-neoplastic Agents and Immunosuppressants: aminoglutethimide, amsacrine, azathioprine, busulphan, chlorambucil, cyclosporin, dacarbazine, estramustine, etoposide, lomustine, melphalan, mercaptopurine, methotrexate, mitomycin, mitotane, mitozantrone, procarbazine HCl, tamoxifen citrate, testolactone.

Anti-protazoal Agents: benznidazole, clioquinol, decoquinate, diiodohydroxyquinoline, diloxanide furoate, dinitolmide, furzolidone, metronidazole, nimorazole, nitrofurazone, omidazole, tinidazole.

Anti-thyroid Agents: carbimazole, propylthiouracil.

Anxiolytic, Sedatives, Hypnotics and Neuroleptics: alprazolam, amylobarbitone, barbitone, bentazepam, bromazepam, bromperidol, brotizolam, butobarbitone, carbromal, chlordiazepoxide, chlormethiazole, chlorpromazine, clobazam, clotiazepam, clozapine, diazepam, droperidol, ethinamate, flunanisone, flunitrazepam, fluopromazine, flupenthixol decanoate, fluphenazine decanoate, flurazepam, haloperidol, lorazepam, lormetazepam, medazepam, meprobamate, methaqualone, midazolam, nitrazepam, oxazepam, pentobarbitone, perphenazine pimozide, prochlorperazine, sulpiride, temazepam, thioridazine, triazolam, zopiclone.

β-Blockers: acebutolol, alprenolol, atenolol, labetalol, metoprolol, nadolol, oxprenolol, pindolol, propranolol.

Cardiac Inotropic Agents: amrinone, digitoxin, digoxin, enoximone, lanatoside C, medigoxin.

Corticosteroids: beclomethasone, betamethasone, budesonide, cortisone acetate, desoxymethasone, dexamethasone, fludrocortisone acetate, flunisolide, flucortolone, fluticasone propionate, hydrocortisone, methylprednisolone, prednisolone, prednisone, triamcinolone.

Diuretics: acetazolamide, amiloride, bendrofluazide, bumetanide, chlorothiazide, chlorthalidone, ethacrynic acid, frusemide, metolazone, spironolactone, triamterene.

Enzymes:

Anti-parkinsonian Agents: bromocriptine mesylate, lysuride maleate.

Gastro-intestinal Agents: bisacodyl, cimetidine, cisapride, diphenoxylate HCl, domperidone, famotidine, loperamide, mesalazine, nizatidine, omeprazole, ondansetron HCL, ranitidine HCl, sulphasalazine.

Histamine H,-Receptor Antagonists: acrivastine, astemizole, cinnarizine, cyclizine, cyproheptadine HCl, dimenhydrinate, flunarizine HCl, loratadine, meclozine HCl, oxatomide, terfenadine, triprolidine.

Lipid Regulating Agents: bezafibrate, clofibrate, fenofibrate, gemfibrozil, probucol.

Local Anaesthetics:

Neuro-muscular Agents: pyridostigmine.

Nitrates and other Anti-anginal Agents: amyl nitrate, glyceryl trinitrate, isosorbide dinitrate, isosorbide mononitrate, pentaerythritol tetranitrate.

Nutritional Agents: betacarotene, vitamin A, vitamin B2, vitamin D, vitamin E, vitamin K.

Opioid Analgesics: codeine, dextropropyoxyphene, diamorphine, dihydrocodeine, meptazinol, methadone, morphine, nalbuphine, pentazocine.

Oral Vaccines: Vaccines designed to prevent or reduce the symptoms of diseases of which the following is a representative but not exclusive list:

Influenza, Tuberculosis, Meningitis, Hepatitis, Whooping Cough, Polio, Tetanus, Diphtheria, Malaria, Cholera, Herpes, Typhoid, HIV, AIDS, Measles, Lyme disease, Travellers Diarrhea, Hepatitis A, B and C, Otitis Media, Dengue Fever, Rabies, Parainfluenza, Rubella, Yellow Fever, Dysentery, Legionnaires Disease, Toxoplasmosis, Q-Fever, Haemorrhegic Fever, Argentina Haemorrhagic Fever, Caries, Chagas Disease, Urinary Tract Infection caused by *E.coli*, Pneumoccocal Disease, Mumps, and Chikungunya.

Vaccines to prevent or reduce the symptoms of other disease syndromes of which the following is a representative but not exclusive list of causative organisms:

Vibrio species, Salmonella species, Bordetella species, Haemophilus species, *Toxoplasmosis gondii*, Cytomegalovirus, Chlamydia species, Streptococcal species, Norwalk Virus, *Escherischia coli, Helicobacter pylori*, Rotavirus, *Neisseria gonorrhae, Neisseria meningiditis*, Adenovirus, Epstein Barr Virus, Japanese Encephalitis Virus, *Pneumocystis carini*, Herpes simplex, Clostridia species, Respiratory Syncytial Virus, Klebsielia species, Shigella species, *Pseudomonas aeruginosa*, Parvovirus, Campylobacter species, Rickettsia species, *Varicella zoster*, Yersinia species, Ross River Virus, J.C. Virus, *Rhodococcus equi, Moraxella catarrhalis, Borrelia burgdorferi* and *Pasteurella haemolytica*. Vaccines directed to non-infections immuno-modulated disease conditions such as topical and systematic allergic conditions such as Hayfever, Asthma, Rheumatoid Arthritis and Carcinomas.

Vaccines for veterinary use include those directed to Coccidiosis, Newcastle Disease, Enzootic pneumonia, Feline leukaemia, Atrophic rhinitis, Erysipelas, Foot and Mouth disease, Swine, pneumonia, and other disease conditions and other infections and auto-immune disease conditions affecting companion and farm animals.

Proteins, Peptides and Recombinant drugs: insulin (hexameric/dimeric/monomeric forms), glucagon, growth hormone (somatotropin), polypeptides or their derivatives, (preferably with a molecular weight from 1000 to 300,000), calcitonins and synthetic modifications thereof, enkephalins, interferons (especially Alpha-2 interferon for treatment of common colds), LHRH and analogues (nafarelin, buserelin, zolidex), GHRH (growth hormone releasing hormone), secretin, bradykin antagonists, GRF (growth releasing factor), THF, TRH (thyrotropin releasing hormone), ACTH analogues, IGF (insulin like growth factors), CGRP (calcitonin gene related peptide), atrial natriurectic peptide, vasopressin and analogues (DDAVP, lypressin), factor VIII, G-CSF (granulocyte-colony stimulating factor), EPO (erythropoitin).

Sex Hormones: clomiphene citrate, danazol, ethinyloestradiol, medroxyprogesterone acetate, mestranol, methyltestosterone, norethisterone, norgestrel, oestradiol, conjugated oestrogens, progesterone, stanozolol, stiboestrol, testosterone, tibolone.

Spermicides: nonoxynol 9.

Stimulants: amphetamine, dexamphetamine, dexfenfluramine, fenfluramine, mazindol, pemoline.

The precise quantity of active ingredient will depend on the drug selected. However, the active ingredient is generally present in an amount from 0.2 to 95%, normally 1 to 20%, by weight of the composition of the dried dosage form.

The invention is further illustrated by the following Examples which are intended to be illustrative and not limitative. In the following Examples FDDF were prepared and tested in absence of an active ingredient.

EXAMPLE 1

The following formulation was prepared:

| Component | Amount | % by weight |
|---|---|---|
| Amylogum CLS | 5 | 10 |
| Mannitol | 1.5 | 3 |
| Purified Water | 43.5 | 87 |

Amylogum CLS is a starch whose hydroxyl groups have been esterified. It is commercially available from the Avebe U.K., Ltd. of South Huberside, England. The mannitol was supplied by Roquette Ltd. of Kent, England.

The starch was added to the purified water and heated to 60° C. while stirring. The resulting mix was maintained at 60° C. for 10 minutes to effect solution and subsequently cooled to ambient temperature. When the mix had sufficiently cooled, the mannitol was added and stirred until fully dissolved. The mix was dosed into PVC/PVdC blisters with 500 mg fill weights. Units were frozen in a stream of cold nitrogen gas then freeze dried by ramping from −10° C. to +20° C. at a pressure of 0.5 mbar.

EXAMPLE 2

The following formulation was prepared adopting the procedure of Example 1.

| Component | Amount (g) | % by weight |
|---|---|---|
| Perfectagel MPT | 5 | 10 |
| Mannitol | 1.5 | 3 |
| Purified Water | 43.5 | 87 |

Perfectagel MPT is a hydroxypropyl distarch phosphate and is commercially available from Avebe U.K., Ltd.

EXAMPLE 3

The following formulation was prepared.

| Component | Amount (g) | % by weight |
|---|---|---|
| Paselli MD10 | 10 | 10 |
| Mannitol | 3 | 3 |
| Purified Water | 87 | 87 |

Paselli MD 10 is an enzymatically modified starch and is commercially available from Avebe U.K. Ltd.

The water was stirred with a hand-held electronic mixer and the starch and mannitol added, while stirring. No heating was required for this starch. The solution was left stirring for 1.5 hours to equilibrate.

Dispersion of the dosage forms in the mouth was smooth, rapid and had a sweet taste.

EXAMPLE 4

The following formulation was prepared adapting the procedure of Example 3.

| Component | Amount (g) | % by weight |
|---|---|---|
| Avebe MD20 | 10 | 10 |
| Mannitol | 3 | 3 |
| Purified Water | 87 | 87 |

Avebe MD20 is an enzymatically modified starch commercially available from Avebe U.K., Ltd.

The dosage forms prepared in Examples 1 to 4 all gave rapid disintegration times in the mouth of less than 10 seconds.

EXAMPLE 5

Investigation into the Viscosity Profiles of a Number of Modified Starches

Formulations having the following composition were prepared.

| Component | Amount (g) | % by weight |
|---|---|---|
| Modified Starch | 3 | 3 |
| Mannitol | 3 | 3 |
| Purified Water | 94 | 94 |

The modified starches used were:

Paselli Easygel which is a pre-gelatinized di-starch phosphate.

Paselli BC which is a pre-gelatinized acetylated di-starch phosphate.

Paselli WA4 which is a pre-gelatinized purified starch.

All of these modified starches are commercially available from Avebe, U.K., Ltd.

Powders were dry-blended and added to the vortex of the purified water. The mixes subsequently being heated to 50° C. and then homogenized with a Silverson L4R (small head adapter). Batches were allowed to cool to ambient temperatures, while continually stirring. Viscosity measurements were taken after 1 to 3 hours mixing and after 22 hours, using the Haake viscometer at 500 $xs^{-1}$.

Results:

| | Viscosity@500$xs^{-1}$ (mPa.s) | |
|---|---|---|
| Batch Component | Initial | After 24 hours mixing |
| Easygel 3% Mannitol 3% | 48.49 | 51.98 |
| Paselli BC 3% Mannitol 3% | 35.18 | 36.06 |
| Paselli WA4 3% Mannitol 3% | 34.17 | 33.87 |

No significant change in viscosity was observed over a 22 hour period. This is a highly desirable property in the preparation of FDDF's. This property improves the efficiency of production and reduces loses due to waste.

EXAMPLE 6

Comparative Stability Study Between Paselli BC and Gelatin

| | Amount (g) | % by weight |
|---|---|---|
| Gelatin Formulation | | |
| Gelatin | 8.75 | 3.5 |
| Mannitol | 7.50 | 3 |
| Purified Water | 233.75 | 93.5 |
| Modified Starch Formulation | | |
| Paselli BG | 8.75 | 3.5 |
| Mannitol | 7.50 | 3 |
| Purified Water | 233.75 | 93.5 |

Paselli BC is a pre-gelatinized acetylated di-starch phosphate commercially available from Croda Colloids, Ltd. of Cheshire, England. Gelatin Formulation The gelatin and mannitol were added to the vortex of the purified water, and heated to 60° C. to effect solution. The mix was subsequently cooled to 25° C. prior to dosing.

Modified Starch Formulation

The mannitol and Paselli BC were dry-mixed and then gradually added to the vortex of the purified water, at ambient temperatures. The resultant mix was subsequently homogenized using the Silverson L4R (small head adapter) for approximately 1 minute.

Mixes were dosed into PVC/PVdC, 16 mm diameter, 500 mg fill weight blisters using the programmable Hamilton Microlab M dispenser. Blisters were frozen in a stream of cold nitrogen gas before freeze drying by ramping from −10° C. to +20° C. at a pressure of 0.5 mbar.

Units were placed, unsealed, in stability cabinets at 40° C. with a relative humidity of 75% for 20 hours, the diameters of the units being taken after this time.
Results:

| Formulations | Tensile Strength N/mm² | | % of shrinkage |
| --- | --- | --- | --- |
| | 2 hours freezer storage | <24 hours freezer storage | after 20 hours @ 40° C./75% RH |
| Modified Starch | 0.013 | 0.123 | 5.6% |
| Gelatin | 0.151 | 0.163 | 10.2% |

It can be seen that the FDDF using the modified starch had a 50% decrease in the amount of shrinkage over the conventional FDDF containing gelatin. This is an unexpected and surprising result.

EXAMPLE 7

Comparative—Gelatin vs. Modified Starch FDDF

An article entitled "Drug Delivery Products and the Zydis Fast Dissolving Dosage Form" by H. Seagers et al., *J Pharm Pharmacol*. 1998, discusses the problems associated with highly water soluble drugs in a FDDF. Zydis® is the registered trademark of the R. P. Scherer Corporation, Basking Ridge, N.J., USA. Seagers et al. recognize that the dose of water soluble drugs is generally limited to an upper value of about 60 mg per dosage form. The dose is governed by the behavior of the drug during the freezing process and on its drying characteristics. Eutectic mixtures can be formed which may not adequately freeze or might melt at the higher temperatures used in the freeze drying process. It is also possible that the dissolved drug could form an amorphous solid on freezing and that this solid might collapse during the drying process due to sublimation of ice and loss of supporting structure.

The collapse of the structure formed by the water soluble drugs is known to be lessened by the inclusion of a crystal forming excipient. These materials are sometimes also known as matrix forming agents. These materials induce crystallinity and hence rigidity in the amorphous products. Another approach is to bind the water soluble compound to an ion exchange resin to form a water insoluble complex. A further technique is to dose a non-aqueous solution of the active ingredient onto pre-formed placebo FDDF units. The organic solvent is then evaporated and the re-crystallized drug is deposited in the pores of the Zydis matrix.

Another technique known to overcome this problem of high water soluble actives is to reduce the drug to excipient ratio and thereby increase the blister fill weight. This effectively dilutes the affect of the soluble active, by having the same drug dose, but a greater quantity of excipients being present. This potential solution has obvious disadvantages in that it requires greater quantities of excipients, a larger "less patient friendly" dosage form, and a decrease in throughput in the manufacture due to size limitations.

It has also been known that the solubility of a drug can be changed through manipulation of the pH. Reduced solubility is known to facilitate incorporation of a higher dose of the active in a FDDF. One aspect of the present invention resides in the discovery that the use of an essentially gelatin free FDDF which utilizes a modified starch material, can incorporate higher levels of water soluble drugs than the conventional gelatin system. This example is submitted to demonstrate this unexpected result.

In this example, three (3) highly water soluble active ingredients were formulated into a FDDF. These actives water solubilities are shown below:

Diclofenac Sodium—1:30 water
Pravastatin Sodium—1:3 water
Phenylpropanolamine HCl—1:2.5 water The following samples were prepared in accordance with Table 1.

TABLE I (All values are weight %)

| Sample # | Gelatin | Starch (Prejel) | Mannitol | Active/Amount | Water |
| --- | --- | --- | --- | --- | --- |
| 1 | 4% | 0 | 3% | Diclofenac Na 2.5%* | 90.5% |
| 2 | 0 | 4% | 3% | Diclofenac Na 2.5% | 90.5% |
| 3 | 4% | 0 | 3% | Pravastatin Na 2.0% + | 91.0% |
| 4 | 0 | 4% | 3% | Pravastatin Na 2.0% + | 91.0% |
| 5 | 4% | 0 | 3% | Phenylpropanol-amine 2.5% # | 91.0% |
| 6 | 0 | 4% | 3% | Phenylpropanol-amine 2.5% # | 91.0% |

*provided 12.5 mg of active in a 500 mg fill.
+ provided 10.0 mg of active in a 500 mg fill.
provided 12.5 mg of active in a 500 mg fill.

Samples 1, 3 and 5 (the gelatin containing samples) were prepared by adding the gelatin and mannitol to the vortex of the stirred, purified water. The mix was then heated to a temperature of 60° C. (±1° C.) to place the gelatin and mannitol into solution. The solution was subsequently cooled to a temperature of 24° C. (±1° C.) and the required amount of the active material was then added. Each batch was held for a minimum of one (1) hour prior to dosing into the blister packs. Samples 2, 4 and 6 (the modified starch samples) were prepared by adding the starch and the mannitol to a clean, dry beaker and dry mixing the materials with a spatula. The purified water was subsequently added to this mix and homogenized using the Silverson L4R Homogenizer—Small Head Adapter at half speed for a period of two (2) minutes. The recited active material was then added to this solution and left for a minimum of one (1) hour prior to dosing. No heating of these batches was required or undertaken.

Each sample was dosed to a 20 blister pack using a Hamilton Microlab, which delivered 500 mg of the mixture (±2%) into the aluminum blister pockets. The blister packs were then frozen at a temperature of −110° C. using liquid nitrogen at a residence time of 3.2 minutes. The frozen samples were subsequently stored at −25° C. prior to freeze drying. Freeze drying was accomplished using a −10° C. to 10° C. temperature cycle at 0.5 mbar. The samples were dried overnight on the same day as manufacture.

After freeze drying, each pack was removed and inspected. Each sample blister was inspected for cracking. This cracking is visually evident from an inspection of the FDDF and it was determined that 90% of Sample 1 evidenced cracking while 0% was evident for Sample 2 (the modified starch containing comparative). Sample 3, containing the gelatin, evidenced a 45–50% cracking rate whereas the starch-based formula, Sample 4, showed no cracking.

Sample 5 containing 2.5 weight % of phenylpropanolamine and 4 weight % gelatin evidenced a cracking rate of from 60–70%. This means that 60–70% of the 20 blister fills for this sample evidenced cracking and crumbled upon attempted removal from the blister pack. In contrast, the use of the starch in Sample 6 evidenced only a 10–20% cracking rate.

This experiment readily demonstrates that the use of a modified starch in a FDDF allows high levels of highly water soluble actives to be incorporated in the FDDF without experiencing cracking and degradation of physical stability as seen with the conventional gelatin formulation.

EXAMPLE 8

Comparative

From the work conducted in Example 7, it is evident that the use of modified starch in a FDDF allows for higher loading of the dosage form without the occurrence of cracking and/or physical failure. An effort was made to determine how much additional material would be required to prepare a gelatin based FDDF containing the same amount of active ingredient, per dosage form. In essence, this experiment was conducted to determine if gelatin based formulas containing highly soluble actives can be prepared without meltback (absorption of water vapor and degradation of physical stability) and cracking problems. The following formulations were prepared:

TABLE II (All values are weight %)

| Sample # | Gelatin | Mannitol | Active/Amount | Water |
|---|---|---|---|---|
| 7 | 4% | 3% | Declofenac Na 1.67% | 91.33% |
| 8 | 4% | 3% | Pravastatin Na 1.33% | 91.67% |
| 9 | 4% | 3% | Phenylpropanolamine 1.67% | 91.33% |

These samples were manufactured as set forth in Example 7 except that a 750 ml fill was used. Upon removal of the samples from the freeze drying, visual inspection resulted in none of the samples containing cracks. This Example demonstrates that larger dosage units are required if gelatin is used in the preparation of the fast dissolving dosage forms. This unexpected result is advantageous in that the smaller dosage forms utilizing the modified starch will enhance patient compliance and reduce the cost of manufacture.

Industrial Applicability

This invention relates to fast dissolving dosage forms for oral administration. The advantages of fast dispersing dosage forms include the lingual, sublingual or buccal delivery of drugs. The current, most commercially popular form is a rapidly soluble solid dosage form that is made by aliquoting a slurry of therapeutic agent, solvent, gelatin and other excipients into preformed depressions. The liquid is then frozen and the solvent is then removed by sublimation, typically freeze drying. The resulting tablet has an open porous matrix that dissolves rapidly on contact with saliva.

The use of the conventional FDDF's has certain drawbacks such as 1) the use of mammalian-derived gelatin; 2) the limited loading of highly water soluble actives in the FDDF; 3) lack of mechanical strength; 4) unpleasant taste; 5) inability to provide homogeneity to the mix; 6) inability to prevent sedimentation of active particles; and 7) minimal cold water dissolution. The present invention advances the state of the art of FDDF by discovering that certain modified starches can be used to prepare FDDFs that have improved physical stability; an unexpected ability to contain higher loadings of highly water soluble drugs; improved taste; improved physical stability (resistance to moisture uptake and subsequent shrinkage when compared to gelatin matrix systems); and a substantial reduction in the sedimentation rate of active particles in the mixture.

It should be understood that the specification and examples are illustrative but not limitative of the present invention and that other embodiments within the spirit and scope of the invention will suggest themselves to those skilled in the art.

We claim:

1. A fast dispersing solid dosage form designed to release an active ingredient rapidly in the oral cavity characterized in that said dosage form is essentially free of mammalian gelatin and comprises:

a) at least one active ingredient;

b) at least one modified starch at a concentration of from 20 to 90% by weight; selected from the group consisting of starches whose hydroxyl groups have been esterified, hydroxypropyl di-starch phosphate, an enzymatically modified starch, a pregelatinized di-starch phosphate, hydroxyethyl starch, a pregelatinized acetylated di-starch phosphate and a pregelatinized purified starch; and c) at least one matrix forming agent;

wherein said solid dosage form has a disintegration/dispersion time of from 1–60 seconds and is obtainable by removing a solvent from a mixture comprising said active ingredient, said modified starch and said matrix forming agent.

2. The fast dispersing solid dosage form according to claim 1 comprises 50% to 90% by weight of said modified starch.

3. The fast dispersing solid dosage form according to claim 1 wherein the modified starches are readily soluble or dispersible in water at ambient temperature.

4. The fast dispersing solid dosage form according to claim 1 wherein the mixture of the active ingredient, the modified starch and the matrix forming agent exhibits a fairly consistent viscosity over a period of about 24 hours.

5. The fast dispersing solid dosage form according to claim 1 wherein the preferred solvent is water.

6. The fast dispersing solid dosage form according to claim 1 wherein the preferred matrix forming agent is mannitol.

7. The fast dispersing solid dosage form according to claim 1 which may also contain coloring agents, flavoring agents, excipients, multiple therapeutic agents.

8. The fast dispersing solid dosage form according to claim 1 wherein the removal of the solvent from the mixture is preferably carried out by freeze drying.

* * * * *